United States Patent [19]

Beaudoin et al.

[11] 3,936,794
[45] Feb. 3, 1976

[54] EXHAUST GAS SENSOR PROBE

[75] Inventors: Gordon L. Beaudoin; Dante S. Giardini, both of Dearborn Heights; Allen H. Meitzler, Ann Arbor, all of Mich.

[73] Assignee: Ford Motor Company, Dearborn, Mich.

[22] Filed: June 27, 1974

[21] Appl. No.: 483,723

[52] U.S. Cl. .................................... 338/34; 73/23
[51] Int. Cl.² ................................ H01C 13/02
[58] Field of Search .......... 73/23, 27 R; 338/28, 34, 338/229; 324/65 R, 65 P, 71 SN; 23/232 E, 254 R, 254 E; 340/237 R

[56] References Cited
UNITED STATES PATENTS

| | | | |
|---|---|---|---|
| 1,955,897 | 4/1934 | Vertucci | 73/27 R |
| 2,445,073 | 7/1948 | Marette et al. | 338/34 |
| 2,806,991 | 9/1957 | White | 338/34 X |
| 2,961,625 | 11/1960 | Sion | 338/28 |
| 3,320,570 | 5/1967 | Lied | 338/34 |
| 3,436,713 | 4/1969 | Di Noia | 338/28 |
| 3,695,848 | 10/1972 | Taguchi | 73/27 R |
| 3,778,229 | 12/1973 | Webster et al. | 73/27 R |

Primary Examiner—Richard C. Queisser
Assistant Examiner—Stephen A. Kreitman
Attorney, Agent, or Firm—Robert A. Benziger; Keith L. Zerschling

[57] ABSTRACT

An exhaust gas sensor probe and its method of manufacture are disclosed. A tube of ceramic material is arranged to support a resistive type ceramic exhaust gas sensor within the cup-shaped cavity in the end portion of the tube. The tube is also provided with a generally continuous groove around the exterior of the cup-shaped end portion to support a heater wire in close heat conductive relation to the sensor ceramic wafer. The ceramaic tube is fixedly received within a housing which may include for example sufficient electrical connective means in the form of electrical terminals to electrically communicate the sensor and the heater wire to an external source of electrical energy and/or a utilization means. The present invention also provides a heat retaining end cap member having an infrared reflective coating for assisting in the retention of heat for those resistive type sensor ceramics which require an operating temperature substantially higher than the temperature of their normal environment.

In fabricating the ceramic support member of the present invention, a suitable ceramic is extruded to form a length of tubing having a plurality of passages extending therethrough. The green ceramic is then prefired until it is machinable and it is then machined to provide the end portion configuration having the generally cup-shaped sensor wafer support portion with the surrounding heater wire support groove. The tube is then finally fired to form a finished ceramic. The sensor ceramic may thereafter be inserted within the cup-shaped end portion of the support ceramic material.

12 Claims, 8 Drawing Figures

EXHAUST GAS SENSOR PROBE

BACKGROUND OF THE INVENTION

1. Field of the Invention

The present invention is directed to the field of internal combustion engine controllers and more particularly to that portion of the above noted field which is concerned with the provision of exhaust gas sensors for use in analyzing the chemical composition of exhaust gases. More particularly still, the present invention is concerned with an exhaust gas sensor support or probe, which will be capable of withstanding the exhaust gas environment for substantial periods of time without cracking or exhibiting other types of fatigue failure, and with its method of manufacture.

2. Description of the Prior Art

Ceramic exhaust gas sensors of the electrically variable resistance type are known. For example, copending commonly assigned patent application Ser No. 391,424, now U.S. Pat. No. 3,893,230, "Air Fuel Ratio Sensor System" by H. L. Stadler et al. describes one such sensor fabricated from titania ceramic material and copending commonly assigned patent application Ser. No. 463,345— "Air Fuel Ratio Sensor For Air Fuel Ratios In Excess Of Stoichiometry" describes such a sensor fabricated from cobalt monoxide ceramic material. Each of these materials demonstrates an electrical resistance change as a function of the partial pressure of oxygen in the gaseous environment of the ceramic material. The resistance changes may be measured by use of a pair of embedded electrodes. Each of these materials functions best at elevated temperature. However, the optimum operating temperature differs for the particular material. In order to operate the materials at their preferred operating temperature, the ceramic usually incorporates a heating means in the form of a platinum heater wire embedded within, or surrounding, the ceramic material. The embedding of the heater follows from the need to prevent any exothermic reactions from occurring at the surface of the platinum such as the catalyzation of carbon monoxide and the need to embed the resistance sensing leads.

In attempting to develop a sensor configuration which may be used in production as an exhaust gas sensor for automobile combustion engines, difficulties have been encountered in the laboratory in mounting the sensitive sensor ceramic material to a support or probe member in such a way that the sensor is reliably operable for periods of time sufficient to meet the demands of automotive production. The presently utilized method comprises bonding or cementing the sensor ceramic directly to a support ceramic with the electrical leads passing through the bonding material.

Sensor problems have arisen due to a variety of causes. In testing, sensor ceramics have become disunited from their support member. Also, vibrations induced by normal engine operation have operated to fracture the electrical wires at the surface of the ceramic sensor body. These problems are believed to stem, at least in part, from the fact that the resistive type ceramic exhaust gas sensor materials require a high degree of porosity in order to provide low response times. This high degree of porosity necessitates a mounting mechanism which places a minimum of the surface area of the sensor ceramic in masked contact with the support member.

A further problem has arisen from the fact that the prior exhaust gas sensor probes have utilized sensor ceramics which have placed a heater element physically within the sensor ceramic. Expansion due to, for example, differential rates of heating has caused nonuniform stresses on the sensor ceramic further complicating the mounting mechanism. It is therefore a specific object of the present invention to provide a probe for supporting an exhaust gas sensor ceramic of the resistive type in such a fashion that fracturing of the ceramic and/or of the electrical connections may be minimized. More particularly, it is an object of the present invention to provide such a structure in which the heating means may be physically distinct and separate from the sensor ceramic. More particularly still, it is an object of the present invention to provide a probe for supporting a wafer of exhaust gas sensor ceramic material which is capable of shielding the wafer of sensor material from direct exhaust gas flow impingement. It is a further object of the present invention to provide such a probe which will support a wafer of exhaust gas sensing material in gas flow contact with an exhaust gas stream while supporting a heating means in heat exchanging relation with the exhaust gas sensor material without being in direct contact with the exhaust gas sensor ceramic. It is also an object of the present invention to provide a support member for a sensor ceramic which permits edge bonding between the ceramics without incorporating the electrical leads in the bond. It is a further object of the present invention to provide for edge bonding which does not require the use of cements or pastes.

As noted hereinabove, two types of resistive exhaust gas sensor ceramics are known to operate at temperatures which differ by several hundred degrees centigrade. It follows from the difference in temperature requirements that substantial differences in the sensor ceramic support mechanism can be expected. It is therefore a further object of the present invention to provide a ceramic support member for a resistive type exhaust gas sensor ceramic material which may be used with sensor ceramic materials which may require operation at widely different temperatures. It is also an object of the present invention to provide an auxiliary heating mechanism for assisting an exhaust gas sensor ceramic and its support probe to retain sufficient quantities of heat so that the exhaust gas sensor ceramic material may operate with the assistance of the auxiliary means at temperatures substantially in excess of that at which it would operate in the absence of the auxiliary means.

SUMMARY OF THE PRESENT INVENTION

The present invention provides a ceramic support probe for use in conjunction with a wafer of resistive type ceramic exhaust gas sensor material to form an exhaust gas sensor probe. The support member of the probe is comprised of an elongated section of ceramic material having a plurality of passages extending therethrough. One end of the probe material is machined to provide a cup-shaped portion having a relatively continuous groove formed on the outer surface of the cup-shaped portion. The groove may be formed, for example, as a screw thread. The interior side walls of the cup-shaped portion are provided with a pair of longitudinally extending slots which are adapted for wedging receipt of a wafer of the resistive type exhaust gas sensor material. A plurality of connecting passages are provided to extend through the side wall portions of the support member in the vicinity of the base of the cup-shaped portion. A winding of heater wire may be situated within the relatively continuous groove and may communicate with an electrical terminal apparatus for establishing a flow of heater current. The support member is preferably situated within a housing means adapted for attachment to, for example, the exhaust system of an automotive internal combustion engine. In those instances where substantially greater quantities of heat are required in the vicinity of the cup-shaped portion in order to maintain a wafer of ceramic exhaust gas sensor material at an elevated temperature, a ceramic end cap may be placed in surrounding relation to the cup-shaped portion and may be provided with an infrared reflective layer in the form of for example, a metallic coating. This coating may be placed on either the interior or the exterior of the end cap.

DETAILED DESCRIPTION OF THE PREFERRED EMBODIMENT

Figure 1:
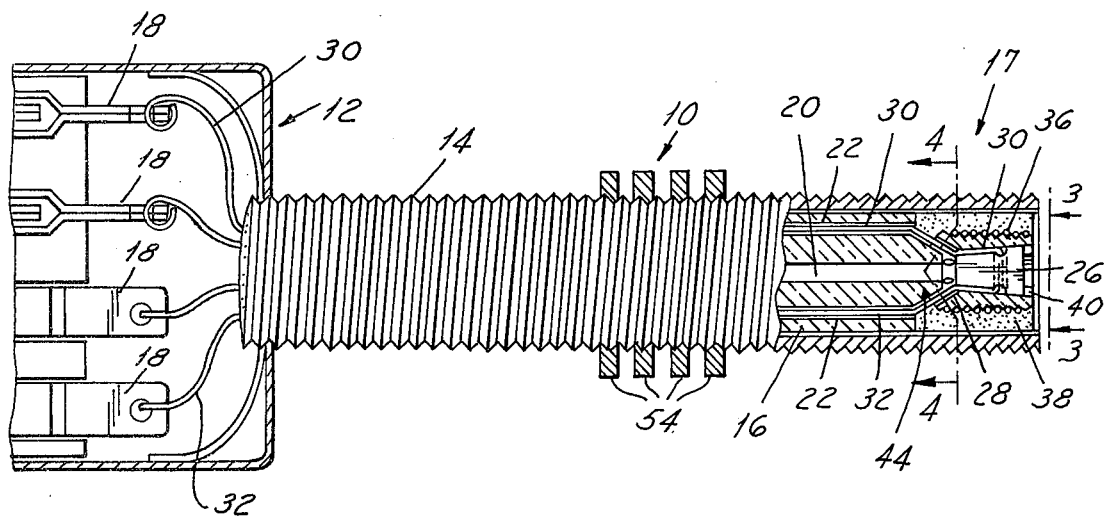
FIG. 1 is an elevational view, partly in section and partly broken away showing an exhaust gas sensor probe fabricated in accordance with the teachings of the instant invention.

Referring now to FIG. 1, an exhaust gas sensor probe 10, according to the present invention, is illustrated. Probe 10 includes an electrical terminal means 12, a housing sleeve means 14, and support member 16. Electrical terminal means 12 includes a plurality of electrical contact members 18 which are operative to communicate the exhaust gas sensor probe 10 with, for example, a remotely located source of electrical energy and a remotely located sensor utilization means. By way of example, copending commonly assigned patent application Ser. No. 375,993, now U.S. Pat. No. 3,868,846, — "Circuit For Converting A Temperature Dependent Input Signal To A Temperature Independent Output Signal", filed in the names of Toshimoto Kushida et al., illustrates one such electrical energization and sensor utilization means. As illustrated, the electrical terminal means 12 is the well known Jones plug and in this embodiment represents a form of electrical terminal means suited to laboratory use. Electrical terminal means for automotive vehicle usage are generally well known and any such means may be employed and such implemention is contemplated.

Support member 16 is here illustrated as a ceramic material and is preferably alumina, $Al_2O_3$. As illustrated, support member 16 extends in a longitudinal direction substantially from the terminal end of housing sleeve means 14 to the opposite, sensor, end 17 of housing sleeve means 14. Support member 16 is provided with a central passage 20 and a plurality of surrounding electrical conduit passages 22. The sensor end of support member 16 is provided with a generally cup-shaped end portion 24 which is arranged to receive and support a wafer 26 of exhaust gas sensor material, principally of the variable resistive type, which responds electrically to changes in the partical pressure of oxygen. As illustrated in FIG. 1 and as further described hereinbelow with reference to FIG. 3, the interior void of the cup-shaped portion 24 is arranged to communicate directly with central passage 20 and, through the diagonal passages 28, with the surrounding electrical conduit passages 22.

Figure 2:
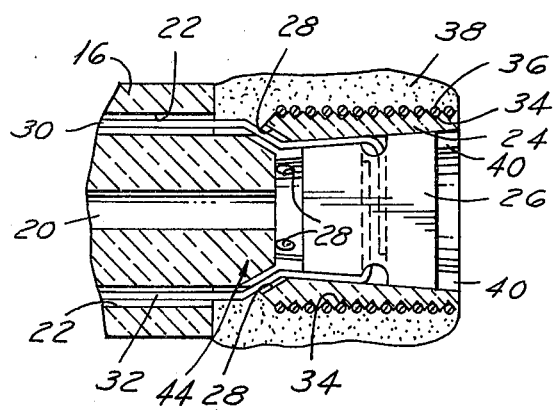
FIG. 2 is an enlarged view of a portion of the probe of FIG. 1 showing the cup-shaped portion in a transverse section.

Referring now to FIGS. 1 and 2, and in particular to FIG. 2, sensor wafer 26 is provided with a pair of sensor conductors 30, 32 which communicate through diagonal passages 28 and electrical conduit passages 22 with selected ones of the electrical contact members 18. The outer surface of cup-shaped end portion 24 is provided with a relatively continuous groove 34 which extends along substantially the entire outer surface of cup-shaped portion 24. A heating means 36 is provided in the form of a winding of heater wire disposed within groove 34. The heater wire 36 may be, for example, platinum and is arranged to communicate through others of the plurality of electrical conduit passages 22 with other of the terminal members 18. The interior surface of cup-shaped end portion 24 may be provided with a pair of generally longitudinally directed confronting slots into which wafer 26 may be inserted. In order to retain heater wire 36 within the groove 34 and to shield the heater wire from any catalytic heating effects and corrosion which may be caused by exposure to the exhaust gases an inorganic potting compound 38 such as, for example, Saureisen Cement No. 33, available from Saureisen Corporation or other suitable refractory cement may be used. Other suitable cements include Al 23 cement, an aluminum oxide cement available from Ventron Corporation and Ceramabond cement available from Aremco Products, Incorporated.

Figure 3:
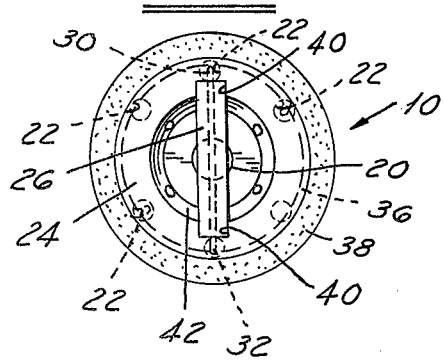
FIG. 3 is a view of the end of the cup-shaped portion of the probe according to the present invention.

Referring now to FIGS. 2 and 3, and particularly to FIG. 3, an end view of probe 10 is shown. As can be seen from these views, the wafer of sensor material 26 is received within a pair of slots 40 formed in the side wall 42 of the cup-shaped end portion 24. Sensor conductors 30, 32 are shown (in phantom lines in FIG. 3) extending from two of the electrical conduit passages 22 (shown in FIG. 3 in phantom line) into the sensor wafer 26. The heating coil 36 is shown (in phantom line in FIG. 3) in surrounding relationship to wafer 26 and is situated within groove 34. Heater wire 36 is shown communicating with a further pair of surrounding passages 22. Due to the truncated wedge shape of wafer 26 and the matching taper of slots 40, the sensor conductors 30, 32 may be slightly deformed during insertion of the wafer 26 within slots 40 by wedging action. This slight deformation may serve to retain wafer 26 with the slots 40. Furthermore, during the life of the probe 10, the ceramic materials of the wafer 26 and support member 16 will fuse and fracture producing a large plurality of interlocking fingers of ceramic material to further assist in holding wafer 26 within the cup-shaped end portion 24.

Figure 4:
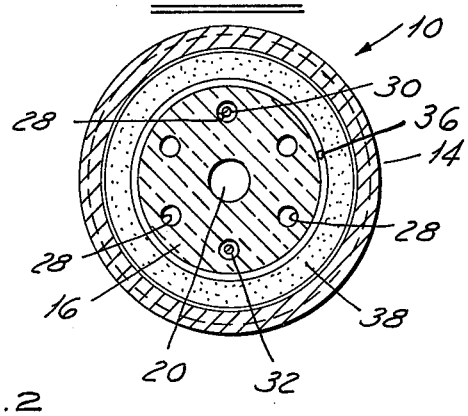
FIG. 4 is a sectional view of the probe according to the present invention, taken along section line 4—4 of FIG. 1.

Referring now to FIG. 4, a sectional view of a portion of the support member 16 taken along section line 4—4 of FIG. 1 is shown. The plurality of connecting passages 28 are shown to extend through the narrowed portion 44 of support member 16. It will be apparent that passages 28 need not be complete and may be simple grooves in the neck of the narrowed portion 44 of support member 16. The potting compound 38 is shown in place between support member 16 and housing sleeve means 14.

Figure 5:
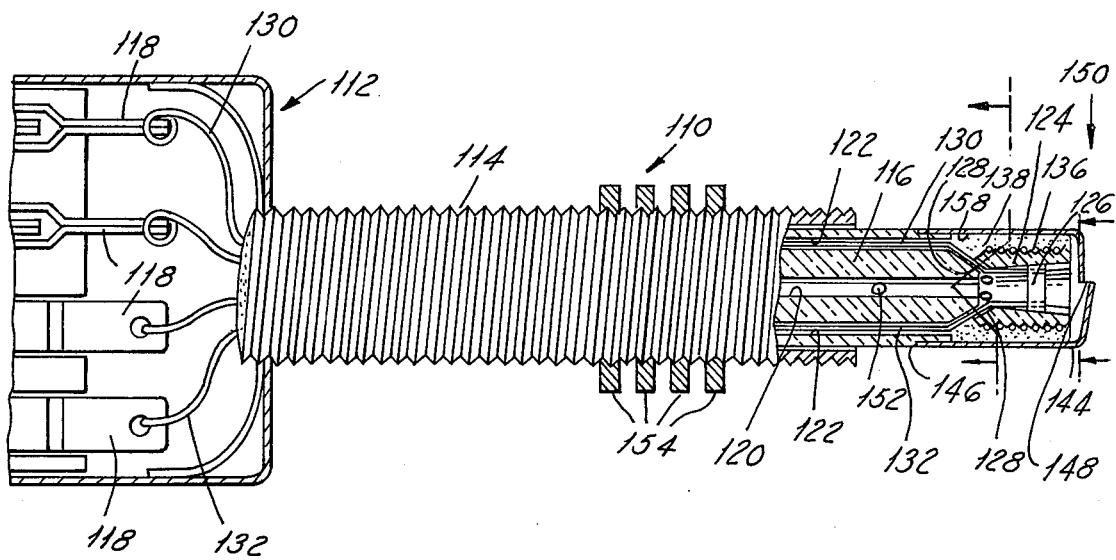
FIG. 5 is an elevational, partly sectioned, partly broken away, view of an exhaust gas sensor probe fabricated according to the teachings of the present invention and intended for use with an exhaust gas sensor element requiring a higher operational temperature than that of the FIG. 1 illustration.
Figure 6:
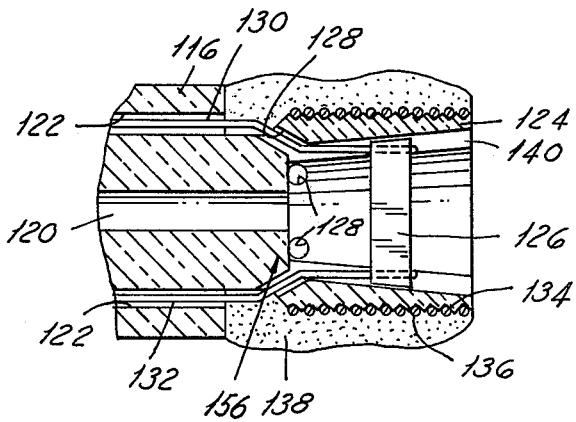
FIG. 6 is an enlarged view of a portion of the probe of FIG. 5 showing the cup-shaped portion in transverse section.

Referring now to FIG. 5, an alternative embodiment of an exhaust gas sensor probe 110 according to the present invention, intended for use with an exhaust gas sensor ceramic operative at higher temperature is illustrated. The probe 110 includes an electrical terminal means 112, a housing sleeve means 114 and support member 116. As with the probe 10 of FIG. 1, the electrical terminal means 112 includes a plurality of electrical contact members 118 and is fixedly attached to the housing sleeve means 114. Support member 116 is received within sleeve means 114. A slight gap is provided between the outer surface of support member 116 and the inner surface of sleeve means 114 to provide for differential rates of expansion in the presence of heating. Support member 116 is provided with a central passage 120 and a plurality of longitudinally extending electrical conduit passages 122 surrounding central passage 120. Support member 116 is also provided with a generally cup-shape end portion 124 which is arranged to open longitudinally away from the main body of support member 116. As illustrated in FIGS. 5 and 6, a wafer 126 of ceramic exhaust gas sensor material is received within the cup-shaped end portion 124. A plurality of diagonal connecting passages 128 are illustrated diagonally interconnecting the interior of cup-shaped portion 124 with the electrical conduit passages 122. As is more clearly illustrated in FIG. 6, the sensor wafer 126 is provided with a pair of electrical leads 130, 132 which communicate the wafer 126 with selected ones of the electrical contact members 118 through connecting passages 128 and electrical conduit passages 122.

With reference to FIGS. 5 and 6, and in particular to FIG. 6, the outer surface of cup-shaped end portion 124 is provided with a relatively continuous groove 134. A heating means in the form of heater wire 136 is situated within the groove 134. An inorganic potting compound or refractory cement 138, such as one of the previously mentioned cements, is situated in generally surrounding relationship to the heater wire 136 and is operative to maintain the heater wire in proper relation with respect to cup-shaped end portion 124 while protecting heater wire 136 from handling damage and from the effects of direct exposure to the exhaust gases.

Figure 7:
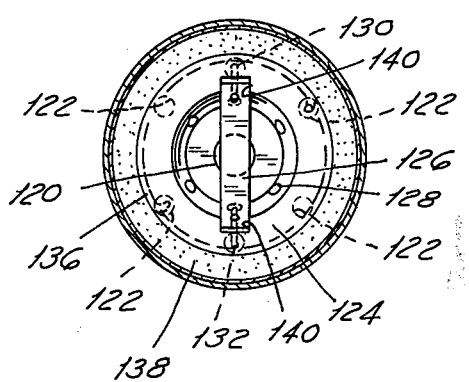
FIG. 7 is a view of the end of the cup-shaped portion of the probe of FIG. 5.

Referring now to FIGS. 6 and 7, wafer 126 can be seen to be inserted within a pair of confronting, longitudinally extending grooves 140 placed in the side wall 142 of cup-shaped portion 124. Electrical leads 130, 132 are shown to extend into, and terminate within, the wafer 126 by phantom lines.

Referring again to FIG. 5, the housing sleeve means 114 are shown to extend a substantial distance in the longitudinal direction along support member 116 but to terminate well short of the cup-shaped end portion 124. A cap member 144 is positioned over the end portion 124 so as to engage a shoulder 146 of support member 116. Cap member 144 is provided with an aperture 148 which is arranged so as to expose the interior of cup-shaped portion 124 to a portion of the exhaust gas stream. Cap member 144 is preferably formed of a ceramic material having a coefficient of expansion compatible with that of the ceramic material selected for support member 116 and may be formed of the same ceramic material. Cap member 144 is operative to inhibit radiation and conduction heat losses from potting compound 138 and heater wire 136 and, to accomplish this objective, may be coated with a thin layer of metallic material having a dielectric constant substantially different from that of the end cap material. For example, a platinum paste having a dielectric constant differing significantly from that of the ceramic end cap 144 will cause infrared reflection to occur at the interface layer between cap 144 and the metallic coating and substantial quantities of heat will be retained. The layer may be provided on either the interior or the exterior surface of end cap 144 depending upon the material selected and its reaction to the exhaust gas environment.

In the embodiment illustrated in FIG. 5, aperture 148 is formed to open in a transverse direction such that an exhaust gas stream flowing in the direction of arrow of 150 will force a small stream of gas to enter aperture 148 and to flow across the surface of wafer 126. This flow of exhaust gases will enter central passage 120 and may be exhausted from central passage 120 by one or more cross passages such as at 152. The cross passages 152 may be arranged at generally right angles to exhaust flow 150 and may extend through support member 116 intermediate the ends of sleeve means 114 and end cap 144. By being generally perpendicular to the exhaust flow, an aspirating effect will occur to facilitate the flow of exhaust gases across the surface of wafer 126.

Referring now to FIGS. 1 and 5, sleeve means 14, 114 are provided with a plurality of fin members 54, 154. These fin members provide for radiation of heat energy to protect the electrical terminal means 12, 112 while providing a convenient mechanism to control the depth of penetration of the probe, 10, 110 within the associated exhaust system of an internal combustion engine so that sensor wafers 26, 126 will be properly positioned at the approximate center of the associated exhaust gas conduit. While sleeve means 14, 114 are shown as comprising a threaded cylindrical member, it will be appreciated that other housing configurations are contemplated. For example, a conventional spark plug sleeve may also be utilized.

Figure 8:
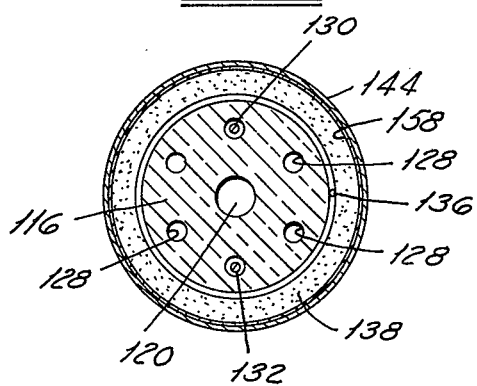
FIG. 8 is a sectional view of the probe of the present invention, taken along section lines 8—8 of FIG. 5.

Referring now to FIG. 8, a sectional view taken along section line 8—8 of FIG. 5 is shown. This view illustrates the diagonal connecting passages 128 which extend through narrowed portion 156 of support member 116. End cap 144 is illustrated in this view as including a thin metallic coating as at 158.

The support members 16, 116 according to the present invention are quite similar and may be fabricated in identical fashion. As illustrated in FIG. 5, support member 116 is provided with an abutment shoulder 146 for receipt of the cap member 144 and this abutment shoulder may be provided by an additional machining step in manufacturing support members 16, 116. In fabricating support members 16, 116, for example support member 16, a relatively liquid body of raw ceramic material which may be for example alumina is extruded through a proper extrusion die to form a multi-passaged, generally cylindrical, rod or tube of raw ceramic material. The ceramic material of the support members 16, 116 is selected to be compatible with the temperature environment of the probe and relatively inert with respect to the exhaust gas constituents and the ceramic of wafers 26, 126. Alumina ceramic is presently preferred on the basis of compatability and cost. This rod or tube may be provided with a length which is substantially equal to that required for probe 10. The elongated tube of ceramic material is then prefired at an elevated temperature for a period of time sufficient, considering the magnitude of the elevated temperature, to produce a machinable green ceramic.

The green ceramic tube is thereafter placed in a machining fixture and the diameter of one end of the tube is reduced from the starting diameter, which may be just slightly larger (to allow for a predictable shrinkage on the order of about fifteen percent) than the inner diameter of sleeve means 14, to provide for the formation of narrowed portion 44 and of the outer surface of cup-shaped portion 24 while the machining of cup-shaped portion 24 is being accomplished. The inner surface of cup-shaped portion 24 may be provided, for example, by drilling to expand the size of central passage 20. Alternatively, both the interior of cup-shaped portion 24 and the central passage 20 may be formed by a drilling process and the electrical conduit passages 22 may also be so formed. Preferably, the interior of cup-shaped portion 24 is a truncated cone.

The next step may comprise forming the transversely disposed, confronting, longitudinally extending sensor receiving slots 40 on the inner wall of cup-shaped portion 24 by use of a suitable cutting tool. These slots 40 should be angled so as to intersect, if extended, at central passage 20 interiorly of support member 16. Connecting passages 28 may be drilled through the side wall of support member 16 to intercommunicate the conduit passages 22 with the interior of cup-shaped portion 24. At the completion of the various machining and drilling steps to provide for the desired configuration of the cup-shaped portion 24 and the various passages communicating therewith, the tube, now comprising a green ceramic version of support member 16, may be committed to final firing. Thereafter, probe 10 may be assembled by inserting the sensor wafer 26 in slots 40 and the conductors 30, 32 in the appropriate passages, situating heater wire 36 in groove 34, bonding support member 16 in the sleeve means 14 and making the necessary electrical connection within electrical terminal means 12. The potting compound 38 may then be added. In addition, a small amount of potting compound 38 may be added to the outer portion of slots 40 to close the slots to further assist in holding the wafer 26 in place.

In those instances where the ceramic selected for support members 16, 116 is alumina ($Al_2O_3$), the prefiring may occur at a temperature of about 1300°F for a period of about 1 hour and the final firing may be conducted at a temperature of about 2700°F for about 2 hours.

Where it is desired to form a support member 116 for use in the higher temperature environment required by a sensor wafer 126 formed of cobalt monoxide ceramic material, the machining step may also include machining of the main body of support member 116 to form the shoulder 146 for receipt of cap member 144 and the step of drilling may also include the step of drilling the cross passages 152.

It will thus be seen that the present invention readily accomplishes its stated objectives. A support member for supporting an exhaust gas sensor is formed which may be used with either a titania or cobalt monoxide based sensor material and which only requires very slight configuration modifications depending on its intended usage. The support member may be readily formed by conventional ceramic and ceramic machining techniques. By providing edge support along two edges of the sensor ceramic material, a thinner sensor ceramic may be fabricated thereby improving the potential response time for the ceramic material by assuring an increase in the gas transport time to enter and fill the various pores of the ceramic material. Furthermore, the wedging action of the wafer in the slots avoids the need for cementing while, in combination with the support provided along opposed edges of the sensor, inhibiting any vibration induced motion or flexing of the electrical leads. The heating means may also be removed from the wafer 26 without exposing it to the deleterious effects of exposure to the exhaust gases. While the heater means is now more remote from the variable resistance zone of primary interest, it is situated so as to be of substantially greater extent so that the heating function is not seriously or adversely effected and the sensor wafer may be of reduced mass and thickness. By providing a ceramic support construction which places the ceramic material at the center of, and not in contact with, a generally helically formed heater wire, the ceramic may be maintained at the desired elevated temperature with lower expenditures of heater wire energization energies and the need for additional wires formed in the sensor ceramic is avoided. Furthermore, by providing the end cap using well known refractory techniques for retaining heat, a wafer of sensor material may be maintained at a greatly elevated temperture with far less expenditure of electrical energy in the heater wire.

We claim:

1. A probe for inserting a wafer of exhaust gas sensor ceramic material into the exhaust gas flow system of an internal combustion engine, comprising in combination:

an elongated ceramic support member having a plurality of generally longitudinally directed passages extending therethrough and a cup-shaped end portion arranged to open longitudinally away from said passages;

said cup-shaped portion having a pair of generally longitudinally directed slots on the inner surface thereof defining means for receiving and supporting a wafer of exhaust gas sensor ceramic materials;

a generally continuous groove formed about the outer periphery of said cup-shaped portion and extending along substantially the entire length of said cup-shaped portion;

housing means fixedly attached to the exterior portion of said support member and including means for mounting the housing to an exhaust gas system so that the cup-shaped portion of the support member extends into the interior of the exhaust gas system;

electrical terminal means attached to said housing so as to be exterior to the exhaust gas system when said housing means is attached to an exhaust gas system;

electrical heater wire means received within said groove for heating the interior of the cup-shaped portion and arranged to electrically communicate through at least a portion of said plurality of support member passages with said electrical terminal means.

2. The probe according to claim 1 wherein said housing means includes a longitudinally extending portion arranged to surround said support member along a major portion of the length of said support member.

3. The probe of claim 2 wherein said surrounding housing portion is longitudinally substantially coextensive with said support member.

4. The probe of claim 2 including further means forming an end cap for placement over the cup-shaped end portion of said support member and arranged to engage a portion of said support member longitudinally displaced from said cup-shaped end portion.

5. The probe of claim 4 wherein said end cap includes an infrared reflective layer whereby loss of substantial quantities of heat energy generated by said heater wire means may be avoided.

6. The probe of claim 4 wherein said end cap includes means forming at least one aperture therein to permit a flow of exhaust gases to be established in proximity to the wafer.

7. The probe of claim 6 wherein said support member is provided with at least one aperture, intermediate the ends of said end cap and said surrounding housing portion, in fluid communication with the interior of the cup-shaped end portion of said support member, for permitting a flow of exhaust gases to be established between said support member aperture and said end cap aperture.

8. The probe of claim 1 wherein said support member end portion is arranged to open in a direction substantially transverse to the direction of flow of an exhaust gas stream.

9. The probe of claim 1 including further curable resin potting compound surrounding said support member end portion for protecting said heater wire and for maintaining said heater wire within said groove.

10. The probe of claim 9 wherein said curable potting compound is arranged to leave the opening of said support member end portion unobstructed.

11. The probe of claim 1 including a wafer of exhaust gas sensor ceramic material received within said support means longitudinal slots and a pair of electrical conductor members attached to opposite faces of said wafer and electrically connected to said terminal means whereby changes in the electrical resistance of said wafer, induced by changes in the gaseous environment of the wafer, may be monitored.

12. The probe of claim 11 wherein said wafer is received within said support means longitudinal slots and contacts said cup-shaped end portion along said longitudinally directed slots only, whereby free circulation of gases comprising the gaseous environment about said wafer is permitted.

* * * * *